United States Patent [19]
Wohlgemuth

[11] Patent Number: 6,029,087
[45] Date of Patent: Feb. 22, 2000

[54] CARDIAC PACING SYSTEM WITH IMPROVED PHYSIOLOGICAL EVENT CLASSIFICATION BASED ON DSP

[75] Inventor: Werner Peter Wohlgemuth, Neukirchen, Germany

[73] Assignee: Vitatron Medical, B.V., Dieren, Netherlands

[21] Appl. No.: 09/158,566

[22] Filed: Sep. 22, 1998

[51] Int. Cl.[7] .................................................. A61N 1/37
[52] U.S. Cl. ............................... 607/9; 128/901; 607/26; 600/509
[58] Field of Search .................................. 600/509, 515, 600/516, 517, 518, 519, 521; 607/2, 4, 5, 9, 14, 26, 17; 128/901, 902

[56] References Cited

U.S. PATENT DOCUMENTS

| | | | |
|---|---|---|---|
| 4,509,529 | 4/1985 | Money et al. | 128/708 |
| 4,742,458 | 5/1988 | Nathans et al. | 364/417 |
| 5,010,887 | 4/1991 | Thornander | 128/901 |
| 5,086,772 | 2/1992 | Larnard et al. | 128/419 D |
| 5,271,411 | 12/1993 | Ripley et al. | 600/515 |
| 5,351,696 | 10/1994 | Riff et al. | 128/702 |
| 5,381,803 | 1/1995 | Herleikson et al. | 607/5 |
| 5,388,586 | 2/1995 | Lee et al. | 128/704 |
| 5,427,112 | 6/1995 | Noren et al. | 128/702 |
| 5,782,887 | 7/1998 | van Krieken et al. | 607/25 |
| 5,891,171 | 4/1999 | Wickham | 607/4 |

OTHER PUBLICATIONS

37 Jiapu Pan et al., "A Real–Time QRS Detection Algorithm," *IEEE Transactions On Biomedical Engineering*, vol. BME–32, No. 3, Mar. 1985, pp. 230–236.

Gary M. Friesen, et al., "A Comparison of the Noise Sensitivity of Nine QRS Detection Algorithms," *IEEE Transactions On Biomedical Engineering*, vol. 37, No. 1, Jan. 1990, pp. 85–98.

Lijun Tian et al., "Time Domain Based Algorithm For Detection of Ventricular Fibrillation," *Proceedings—19th International Conference, IEEE–EMBS*, Oct. 30–Nov. 2, 1997, pp. 374–377.

Cuiwei Li et al., "Detection of ECG Characteristic Points Using Wavelet Transforms," *IEEE Transations on Biomedical Engineering*, vol. 42, No. 1, Jan. 1995, pp. 21–28.

Valtino X. Afonso, "Filter Bank–Based Processing of the Stress ECG," *IEEE*, 1995.

(List continued on next page.)

*Primary Examiner*—Kennedy J. Schaetzle
*Attorney, Agent, or Firm*—Thomas F. Woods; Harold Patton; Michael J. Jaro

[57] ABSTRACT

There is provided an implantable cardiac pacing system or other cardiac monitoring system, having an enhanced capability of classifying intracardiac signals through a combination of DSP techniques and software algorithms. The implantable device has one or more DSP channels corresponding to different signals which are being monitored. Each DSP channel provides for amplification of the incoming signal; conversion from analog to digital form; digital filtering of the converted signals to provide filtered signals; operating on the filtered signals to provide slope signals; determining from the filtered and slope signals whenever an intracardiac event has been detected, e.g., R wave, P wave, etc.; and signal processing of the filtered and slope signals for a predetermined analysis interval after threshold crossing, for generating a plurality of signal parameters. The thus generated signal parameters corresponding to a signal are further operated on by a programmable algorithm to classify the detected event based upon the DSP-generated parameters. By this combination of digital signal processing and programmable software coordinated with each DSP channel, enhanced intracardiac signal classification is achieved.

21 Claims, 14 Drawing Sheets

OTHER PUBLICATIONS

V. DiVirgilio et al., "ECG Fiducial Points Detection Through Wavelet Transform," *IEEE,* 1995.

Marcelo R. Risk, "Beat Detection and Classification of ECG Using Self Organizing Maps," *Proceedings—19th International Conference—IEEE/EMBS,* Oct. 30–Nov. 2, 1997, pp. 89–91.

Valtino X. Afonso et al., "Filter Bank–Based ECG Beat Classification," *Proceedings—19th International Conference—IEEE/EMBS,* Oct. 30–Nov. 2, 1997, pp. 97–100.

Ming–Yao Yang, "ECG Events Detection and Classification Using Wavelet and Neural Networks," *Proceedings—19th International Conference—IEEE/EMBS,* Oct. 30–Nov. 2, 1997, pp. 280–281.

Oliver Wieben et al., "Classification of PVCS With A Fuzzy Logic System," *Proceedings—19th International Conference—IEEE/EMBS,* Oct. 30–Nov. 2, 1997, pp. 65–67.

H.H. So et al., "Development of QRS Detection Method For Real–Time Ambulatory Cardiac Monitor," *19th International Conference—IEEE/EMBS,* Oct. 30–Nov. 2, 1997, pp. 289–292.

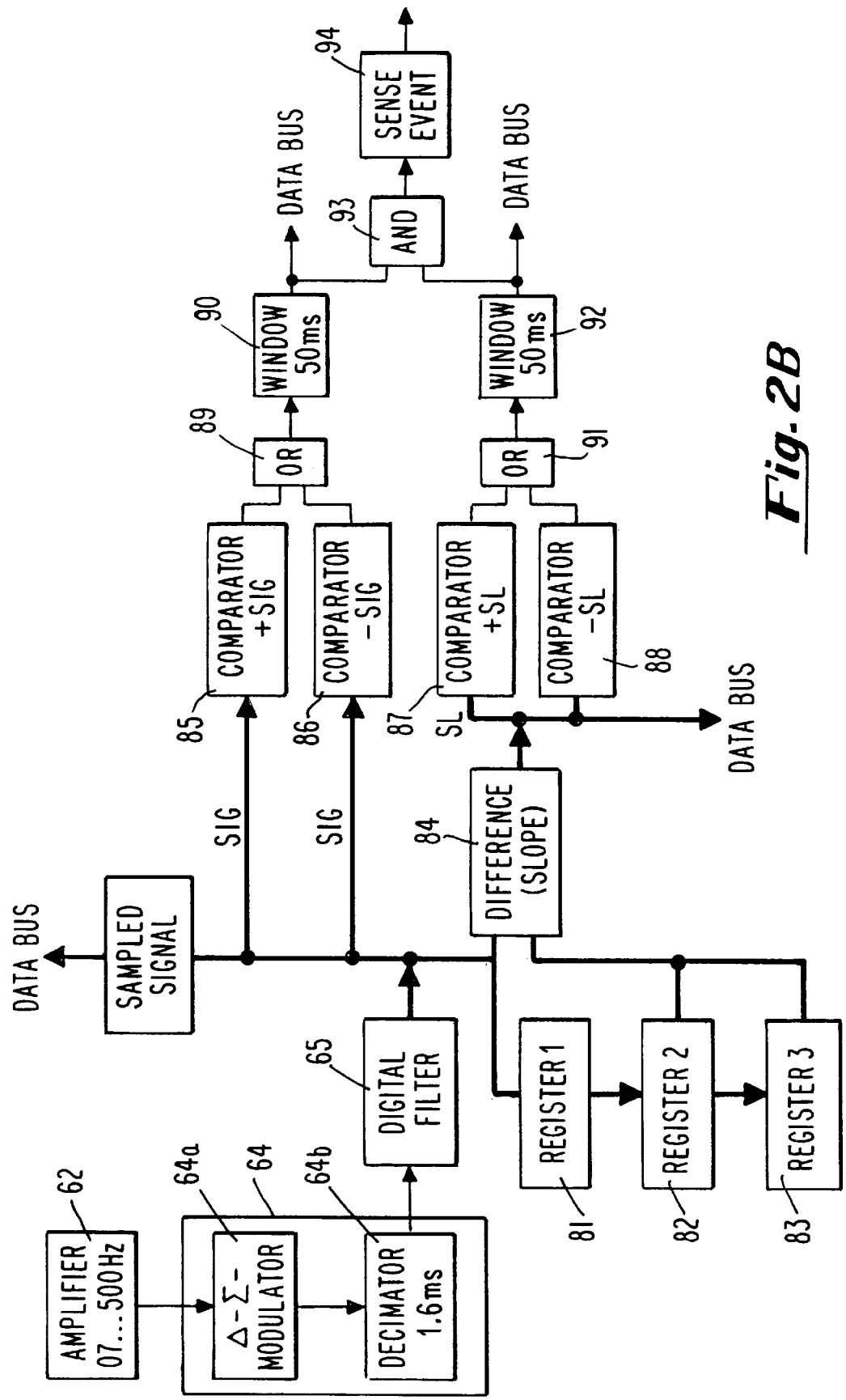

CARDIAC PACING SYSTEM WITH IMPROVED PHYSIOLOGICAL EVENT CLASSIFICATION BASED ON DSP

FIELD OF THE INVENTION

This invention relates to cardiac pacing systems having the capability of recognizing sensed signals, the recognition being based upon characteristics of the sensed signal and, more particularly, such systems which utilize digital signal processing for analysis of sensed signals in combination with a software-based decision algorithm.

BACKGROUND OF THE INVENTION

Implantable cardiac pacemakers have a great need to accurately process sensed signal information, so as to determine when a genuine cardiac signal has in fact been sensed, and then and to accurately identify, or classify the signal. Separating cardiac signals from polarization effects and other noise artifacts has always been a substantial problem, and a great deal of effort has been placed on improving input circuits for this purpose. Additionally, it is recognized that it is important to be able to classify a sensed signal, e.g., determine whether it is a QRS, P-wave, far field R-wave (FFRW), or what. Many prior art techniques have been developed for signal classification, but improvement is still needed. For example, one prior art technique is to establish a variable timing window, and classify the event in terms of the timing of the signal received during window. However, early beats; ectopic signals, etc. can fool such a technique, and noise can still mask the signal which is sensed within window. Other known techniques include morphology analysis, comparisons in the time and frequency domain, etc. While many of these techniques provide reasonably good results, they can involve considerable circuit complexity and frequently do not eliminate the probability of error due to detection of noise or other artifacts.

The advent of digital signal processing (DSP) has provided a tool which can be very useful in the environment of an implanted medical device, e.g., an implanted pacemaker. In DSP technology, the incoming sense signal is converted to a digital signal, e.g., an 8 bit signal at some sample rate. Successive digital signals can be processed with high reliability, in a manner which is essentially hardware-controlled by the DSP circuitry. More recently, DSP technology has advanced so as to provide the possibility of a low current chip which can be used in an implantable pacemaker to provide significant sensed signal processing capability.

The utilization of a DSP chip for an implantable pacemaker makes available an enhanced capability of processing sensed signals, so as to enable more accurate classification of the signal. Such DSP processing, together with a microprocessor and an appropriate signal classification algorithm, provides a powerful tool for accurately sensing and classifying intracardiac signals. In addition to this combined hardware and software capability, there is a need to provide an optimum decision algorithm for using the DSP-generated signal parameters so as to accurately and reliably classify sensed intracardiac signals.

SUMMARY OF THE INVENTION

It is an object of this invention to provide an implantable pacemaker having combined DSP-microprocessor capability for reliably processing and classifying intracardiac signals, so as to provide the pacemaker with reliable cardiac event data. It is a further object to utilize an optimum combination of DSP processing for generating signal parameters, and software for analyzing the DSP-generated signal parameters so as to make reliable signal classifications.

In accordance with these objectives, there is provided an implantable pacemaker system, having a pacemaker and lead, the lead serving to deliver generated pacing pulses to the patient's heart and to pick up and deliver sensed intracardiac signals to the pacemaker. The pacemaker has DSP circuitry, preferably provided on a DSP chip, for receiving the sensed cardiac signals, digitizing them, and obtaining for each sensed signal a predetermined set of parameters from which a signal classification is made. The signal parameters are passed to a microprocessor which contains a classification algorithm for analyzing the parameters and making a classification decision.

In a preferred embodiment, the DSP circuitry determines up to nine parameters for each analyzed signal, each parameter representing a predetermined characteristic of the signal. The DSP circuitry continuously filters the incoming signals and generates the slew rate, or slope of the signal from the filtered signal; and it compares each of the filtered and slope signals to a respective predetermined positive and negative threshold. A sense window of a predetermined time limit, e.g., 50 ms, is started with the first threshold crossing, and a signal is deemed to be sensed only when it has crossed one filtered signal threshold and one slope threshold within the sense window. Whenever a striking signal appears, the DSP logic times out an analysis window of predetermined duration, e.g., 70 ms. The analysis window may be initiated at the time of the first threshold crossing; at the time of a "sense"; or at a software-generated time produced under control of the processor. For each of the filtered signal and the slope signals, a maximum and minimum value is obtained during the analysis window, and a time interval from signal sense to the maximum and minimum for each of these signals is obtained. Additionally, a signal window length from the first crossing of any one of the four thresholds to the last such crossing during the analysis window is generated, providing a ninth parameter.

A separate DSP channel is used for sensing each respective type of signal, and for generating parameters corresponding to such signal. The parameters from each channel are transferred on a data bus to a microprocessor, which is software controlled to classify each sensed signal as a function of one or more of the DSP-generated parameters. The software includes a classification algorithm for each DSP channel, and each algorithm is programmable so that classification for the patient can be optimized for each signal type.

BRIEF DESCRIPTION OF THE DRAWINGS

FIG. 2B is a block diagram showing the DSP components for generating a sense signal;

DESCRIPTION OF THE PREFERRED EMBODIMENTS

Figure 1:
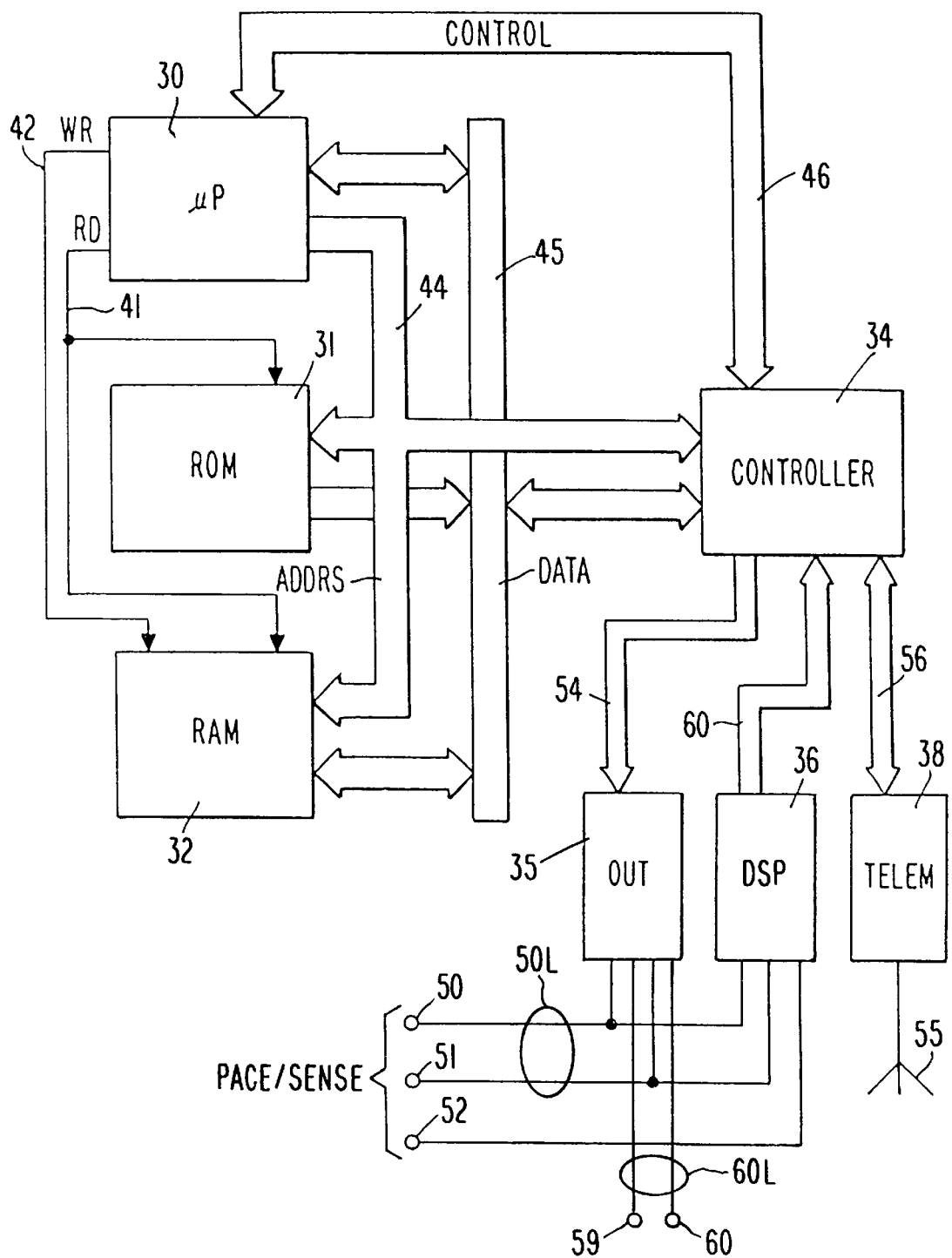
FIG. 1 is a block diagram showing the primary components of an implantable pacemaker in accordance with this invention, illustrating the position of a DSP chip and a microprocessor in the overall scheme of sensed signal processing.

Referring now to FIG. 1, there is shown a functional block diagram of an implantable pacemaker of a type with which the present invention may be practiced. It is to be noted that FIG. 1 is representative of such a pacemaker, and is not limiting in the actual architecture of the pacemaker. It is presented for the purpose of discussing data flow and, in particular, the position of a DSP chip and a microprocessor for purposes of sensing, analyzing and classifying sensed intracardiac signals. Accordingly, FIG. 1 is considered to be exemplary rather than limiting with regard to the present invention. While the invention is disclosed as embodied in a pacemaker, it is likewise applicable to incorporation in a cardioverter, or combined cardioverter pacemaker, cardioverter defibrillator pacemaker, etc. Further, while the discussion of FIG. 1 assumes a single chamber ventricular pacing system, it is to be understood that the invention is applicable to dual chamber and multi-chamber systems, e.g., in a preferred dual chamber embodiment, the DSP chip has three channels, for respective processing of P, R and T wave signals.

The primary elements of the apparatus illustrated in FIG. 1 are microprocessor 30, read only memory 102, random access memory 32, a digital controller 34, output amplifier 35, DSP circuitry 36, and a telemetry/programming unit 38. Read only memory 31 stores the basic programming for the device, including the primary instructions set defining the computations performed to derive the various timing intervals performed by the device. Random access memory 32 serves to store the values of variable control parameters, such as programmed pacing rate, pulse widths, pulse amplitudes, and so forth, which are programmed into the device by the physician. Reading from random access memory 32 and read only memory 31 is controlled by RD-line 41. Writing to random access memory 32 is controlled by WR-Line 42. In response to a signal on RD-Line 41, the contents of random access memory 32 or read only memory 31 designated by the then present information on address bus 44 are placed on data bus 45. Similarly, in response to a signal on WR-line 41, information on data bus 45 is written into random access memory 32 at the address specified by the information on address bus 44.

Controller 34 performs all of the basic timing and control functions of the illustrative pacemaker device. Controller 34 includes at least one programmable timing counter, e.g., initiated on paced or sensed ventricular contractions, for timing out intervals thereafter. This timing counter is used to define the escape intervals for timing generation of pace pulses, as well as for timing the respective durations of the charge and recharge pulse portions of triphasic pulses. Controller 34 triggers output pulses to be generated and delivered from output stage 35, and it generates interrupts on control bus 46 for cyclically waking microprocessor 30 from its sleep state to allow it to perform the required functions. For a single chamber pacemaker output circuit 35 is coupled to electrodes 50 and 51 which are employed both for delivery of pacing pulses and for sensing of cardiac signals. Electrode 50 is typically located on the distal tip end of an endocardial lead 50L, and for ventricular pacing is preferably placed in the apex of the right ventricle; for atrial pacing, of course, it is placed in the patient's atrium. Electrode 51 is preferably a ring electrode, as used with a bipolar lead. Electrode 52 represents the pacemaker housing, which may be used as the indifferent electrode for selected unipolar pacing and/or sensing operations. Of course, for a dual or multi-chamber pacing system, additional electrodes are employed. For example, electrodes 59,60 carried by lead 60L may be used for pacing and sensing in the atrium, while electrodes 50,51 are used in the ventricle. Output circuit 35 is controlled by controller 34 through bus 54 to determine the amplitude and pulse width of the pulse to be delivered and to determine which electrode pair is to be employed to deliver the pulse.

Cardiac signals are sensed at a desired pair or pairs of electrodes; bipolar and/or unipolar sensing may be used. For "combipolar" sensing, a unipolar lead in the atrium and a unipolar lead in the ventricle are used, e.g., the signals are picked up at electrodes 50,59. Sense signals are inputted to DSP block 36, which comprises a number of signal processing channels corresponding to signals of interest. For example, in a dual chamber pacemaker which incorporates P wave processing either for rate control, capture detection or any other reason, there are three channels for respective signal processing of the P, R and T waves. The data resulting from the digital signal processing is transmitted via bus 60 through controller 34 and bus 46 to microprocessor 30, for the signal classification operations, as well as any other necessary calculations.

External control of the implanted device is accomplished via telemetry/control block 38, which allows communication between the implanted device and an external programmer (not shown). Radio communication is typically employed via antenna 55. Appropriate telemetry/programming systems are well known in the art; the present invention is workable with any conventional telemetry/programming circuitry. Information entering the pacemaker from the programmer is passed to controller 34 via bus 56. Similarly, information from the pacemaker is provided to the telemetry block 38 via bus 56, for transmission to the external programmer. Of importance to this invention, the classification algorithms for processing the parameters generated by each DSP channel can be re-programmed in a known manner.

Figure 2A:
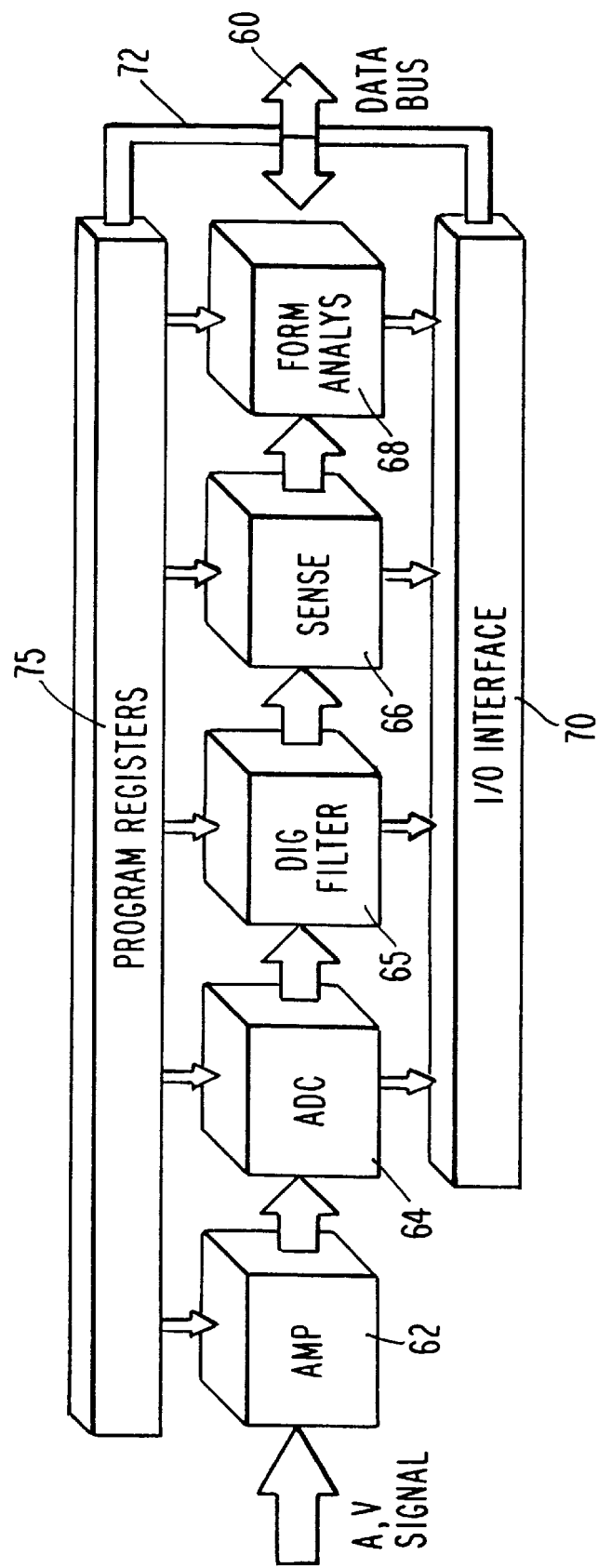
FIG. 2A is a block diagram illustrating the primary functional and structural components of a DSP channel in accordance with this invention.
Figure 3A:
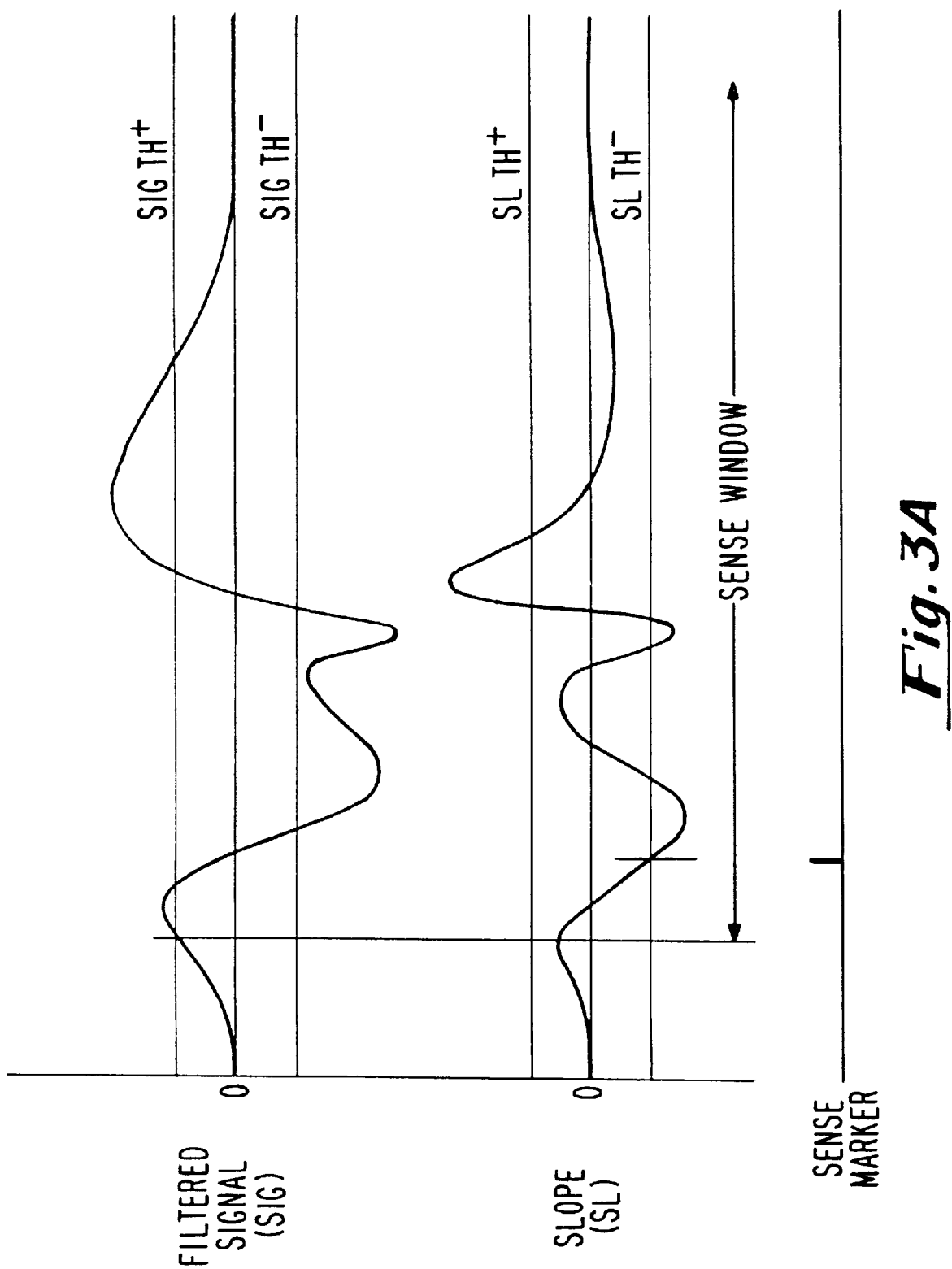
FIG. 3A is a set of curves illustrating a sampled and filtered cardiac signal, a slope signal derived from the filtered signal, and the determination of a sense window and sense marker.

Referring now to FIG. 2A, there is shown a diagram representing the primary components of a DSP chip 36. The chip is manufactured with a chip area of about 20 mm$^2$, and draws about 0.7–1.5 microamps per channel. FIG. 2A shows an atrial (A) or ventricular (V) signal introduced into a DSP channel; it is to be understood that as many similar channels as desired are provided for signal processing of respective signals. The signal, still in analog form, is first passed through an amplifier 62, having a filter characteristic of about 0.7 to 500 Hz. The amplified analog signal is passed into A/D converter 64, for generation of a digital signal. The A/D conversion is suitably done by a delta-sigma modulator, as shown in FIG. 2B, followed by a decimater to provide typically 8-bit bytes at 1.6 ms intervals. The digital signal from block 64 is connected to digital filter 65 which is suitably a digital bandpass filter having a characteristic to eliminate low frequency signal components and the offset of the converter, as well as to take out high frequency artifacts. The output of block 65, referred to as SIG in FIG. 3A, is connected to sense block 66. Sense block 66 obtains the slew rate, or slope of the signal, also hereafter referred to as the SL signal, and then compares both the SIG and SL signals to plus and minus threshold voltages to derive a "sense" signal.

As seen in more detail in FIG. 2B, the output of digital filter 65, in one embodiment, is connected to a series of three registers, Registers 81, 82 and 83 being cascaded so that at each sample the digital signal in Register 1 is passed to Register 2, and the signal in Register 2 is passed to Register 3. The difference is then obtained at difference circuit 84, by taking the difference between either Register 1—which holds the SIG signal—and Register 2; or the difference between Register 1 and Register 3. At block 85 the SIG signal is compared with a positive voltage threshold, and at block 86 the SIG signal is compared with a negative threshold signal. Whenever the SIG exceeds either threshold, an output is passed through OR gate 89, and triggers generation of a window signal of 50 ms duration, shown at block 90. Likewise, the difference or SL signal from block 84 is compared at 87 with a positive threshold and at 88 with a minus threshold, and if either threshold is exceeded, a signal is passed through OR gate 91 to window circuit 92. Whenever there is a first signal through either OR gate 89 or OR date 91, and there follows a signal through the other OR gate within 50 ms, AND circuit 93 produces an output, which is recognized at 94 as a sensed event.

Referring now to FIG. 3A, the upper curve represents the filtered signal (SIG), and the lower signal represents a corresponding slope (SL) signal corresponding to an event which is to be sensed and classified. For each signal, plus and minus threshold values are indicated, i.e., SIG TH+, SIG TH−, SL TH+, and SL TH−. It is seen that in this example, the SIG signal crosses the positive threshold first, and one or two samples later the SL signal crosses its negative threshold. The 50 ms sense window is illustrated as being timed out from the instant of the first threshold crossing. The identification of a sense event by a sense marker is represented on the bottom line, corresponding to the time when both signals had crossed one of their thresholds.

Figure 2C:
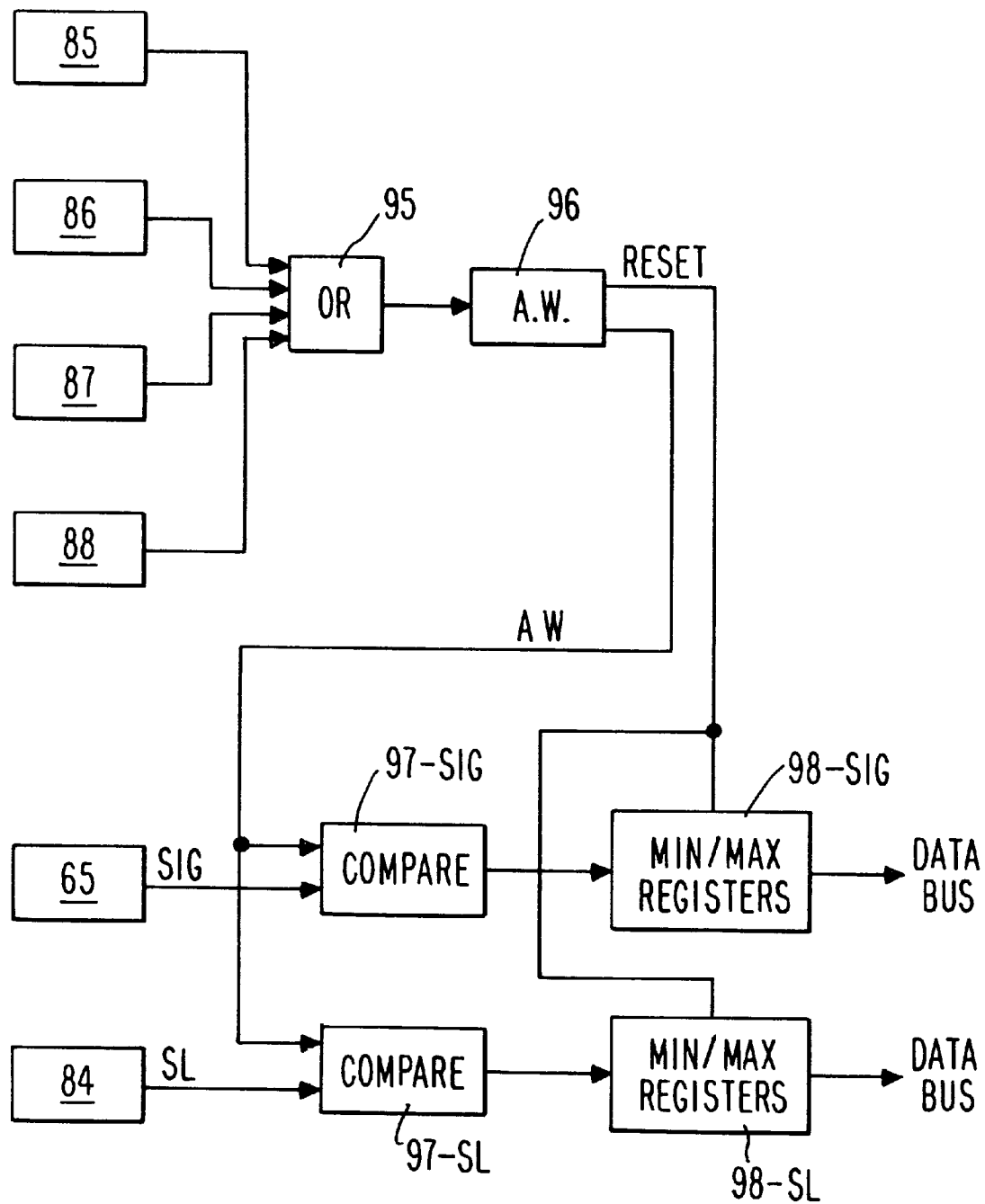
FIG. 2C is a block diagram showing the DSP components for collecting the analysis data.
Figure 3B:
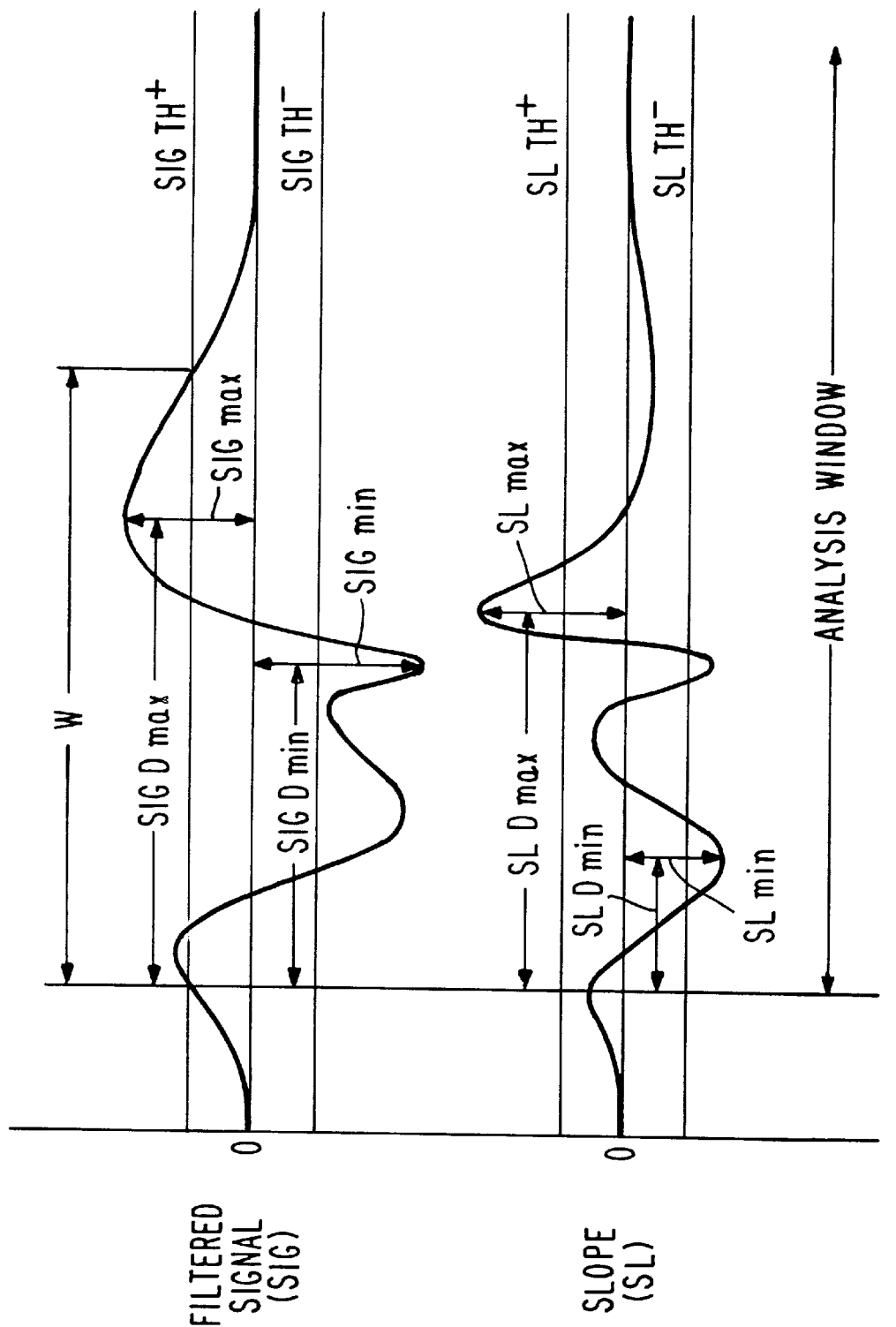
FIG. 3B is a similar set of curves, illustrating the analysis window and the parameters that are obtained for classification of the event.

Referring now to FIG. 2C, there is shown a block diagram of an illustrative circuit corresponding to block 68 of FIG. 2A, titled "form analys". This block is where the DSP circuitry operates during the 70 ms analysis window to extract parameters from the signal under examination, which parameters are shown in FIG. 3B. When the analysis window is active, the SIG and SL values are operated on to obtain the signal parameters that are illustrated in FIG. 3B. Referring first to the filtered signal as illustrated in FIG. 3B, both maximum and minimum values of SIG during the analysis window are obtained; the positive value is indicated as SIGmax and the negative as SIGmin. The time from sense to SIGmax is indicated as SIG Dmax; and the time from sense to SIGmin is indicated as SIG Dmin. Likewise, referring to the SL curve, values of SLmax and SLmin are determined, and the time from sense to each is found, namely SL Dmax and SL Dmin. Additionally, the time from first crossing of a threshold to the last crossing of a threshold is determined as labelled W; in this example W is from the first SIG crossing of the positive threshold to the last SIG crossing of the SIG positive threshold.

Referring again to the illustrated circuit of FIG. 2C, the analysis window is initiated by the first occurrence of the event signal crossing one of the four thresholds.

Thus, the inputs from comparators 85–88, as seen in FIG. 2B, are gated through OR circuit 95, and the first signal gated through initiates the generation of a window signal at circuit 96. The analysis window signal is connected to enable compare circuits 97-SIG and 97-SL. Circuit 97-SIG compares the SIG signal from block 65 with the current values of MIN/MAX registers 98-SIG; and circuit 97-SL compares the SL signal from block 84 with the current values of MIN/MAX registers 98-SL.

The 8-register set, 98-SIG and 98-SL is reset at the start of the analysis window. At each signal sample, the SIG and SL signal samples are separately compared to four respective registers, which correspond to that signal's four respective parameters as seen in FIG. 3B; and new parameter values are written into the corresponding registers. Thus, If SIG<SIG min, then SIG→SIG min , and D→SIG D min;

If SIG>SIG max, then SIG→SIG max, and D→SIG D max;

If SL<SL min, then SL→SL min, and D→SL D min;

If SL>SL max, then SL→SL max, and D→SL D max.

Also, W is recorded as the time from the first crossing of a threshold to the last threshold crossing.

Thus, the parameters are obtained by the DSP circuitry form by continuous operation on each byte of data from the time of the first threshold crossing until the end of the analysis window. The parameters are provided on data bus 60, which is communicated directly through onto bus 46 to microprocessor 30. Note that the output of each of blocks 64, 65, 66 and 68 is connected through I/O interface 70 to a bus 72, which can either connect to data bus 60 or to program registers 75. The registers connect to blocks 62, 64, 64, 66 and 68, and serve a variety of purposes, such as programming amplifier sensitivity, programming threshold levels of the sense block, etc.

Figure 4:
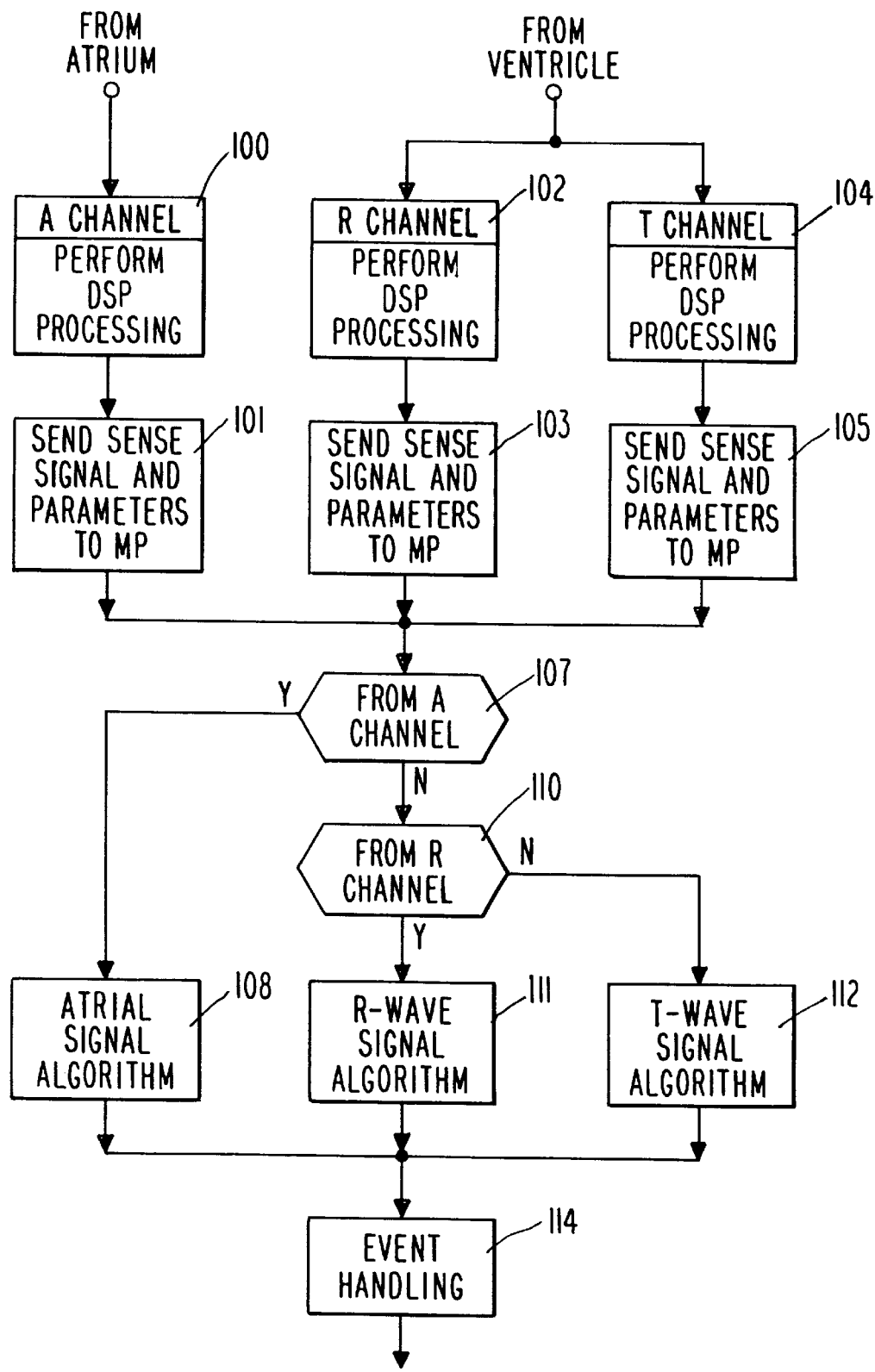
FIG. 4 is a simplified flow diagram showing plural channels of the DSP chip, each operating in combination with a respective signal classification algorithm, and illustrating the primary steps in sensing, classifying and utilizing intracardiac signals in accordance with this invention.

Referring now to FIG. 4, there is presented a flow diagram which gives an overall perspective on the processing operations carried out in a pacemaker system in accord with this invention. As illustrated at block 100, an incoming analog signal which has been sensed in the atrium is inputted to the A channel of the DSP chip. The A channel is programmed with thresholds corresponding to signals sensed in the atrium. The received signal is operated on as discussed above, namely it is amplified; converted from A to D; digitally filtered; the slope signal is obtained; a sense signal is obtained if a signal is in fact present; and the form analysis is performed to obtain the parameters, e.g., up to nine parameters, as set forth above. Following these DSP operations, a sense signal and the parameters are sent to the microprocessor 30, as indicated at block 101. If the signal has come from the ventricle, it is connected to the R channel (102) of the DSP chip and also to the T channel (104). The R channel is programmed with thresholds appropriate to R waves, and performs the same DSP functions as the A channel; the resulting sense signal and parameters are sent to the microprocessor, as shown at block 103. The T channel is programmed with thresholds corresponding to T waves, and likewise performs the functions as shown in FIG. 2A, and thereafter sends data to the microprocessor as shown at 105. The microprocessor determines the channel from which the data has been sent, at 107 and 110, and selects the corresponding algorithm for signal classification. For a signal from the A channel, the data is operated on with an atrial signal algorithm, shown at 108; for a signal from the R channel, the data is operated on with an R wave signal algorithm 111; and for a signal from the T channel, the signal is operated on by T wave algorithm 112. Following a signal classification from any one of the channels, the microprocessor goes on to the appropriate event handling at 114, i.e., predetermined logical steps follow the detection of each respective type of signal. See, for example, U.S. Pat. No. 5,782,887, issued Jul. 21, 1998, incorporated herein by reference, which provides examples of V sense, A sense and T wave event handling.

It is important to note that each microprocessor classification algorithm is programmable. For a given channel which is to process atrial or ventricular signals, any combination of the nine parameters can be utilized, and they are weighted relative to each other. Thus, there is provided a flexibility, wherein the DSP chip very efficiently obtains the signal parameter data, while the software algorithm for each respective channel is optimally programmed to carry out the calculations for determining signal classification.

Figure 5A:
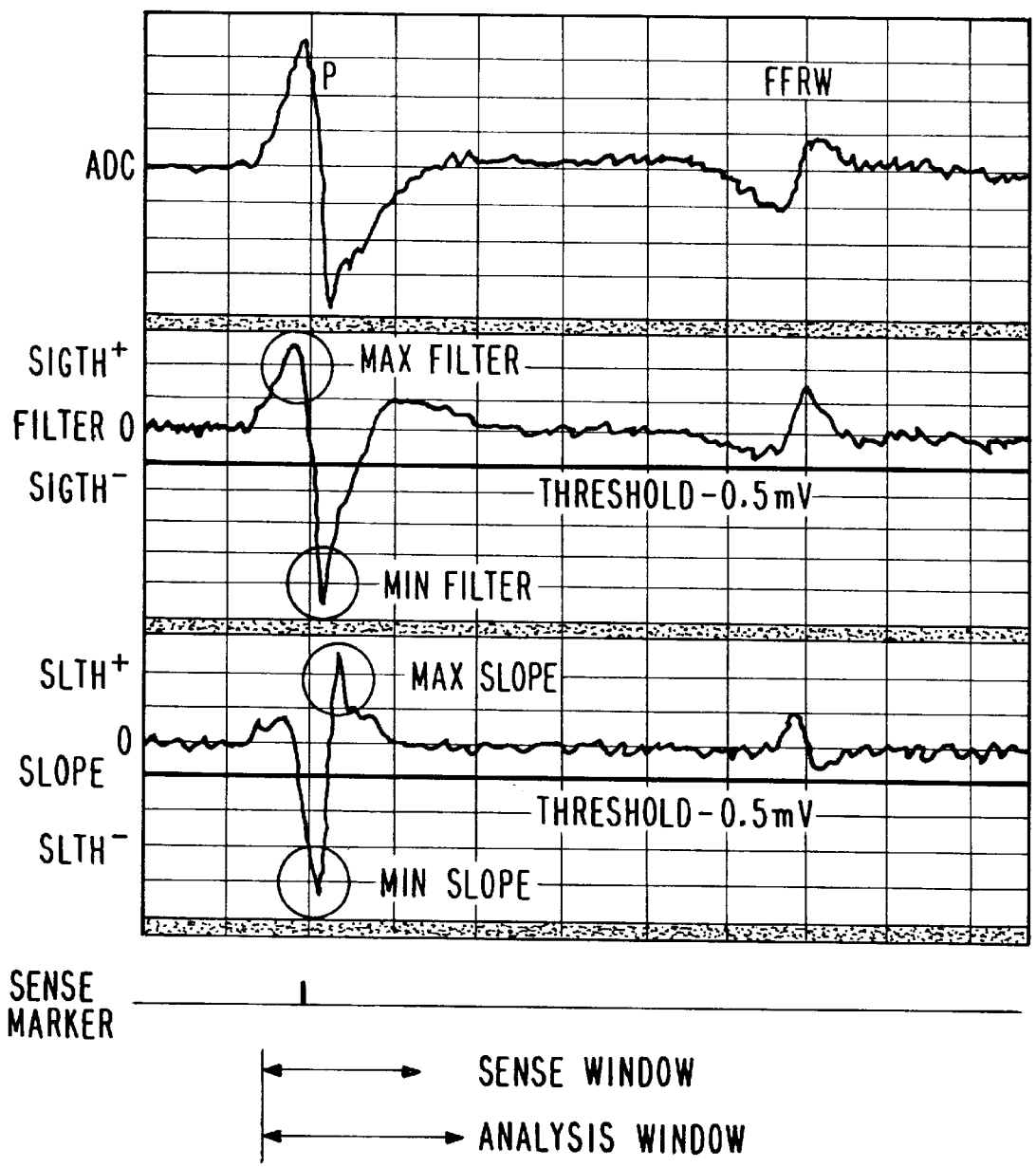
FIG. 5A is a series of curves showing an atrial signal as converted into digital form; the filtered signal; the slope of the filtered signal; and markers indicating when a signal is sensed and the end of the analysis window.

Referring now to FIGS. 5A–5D, there is illustrated the operation of a channel of the DSP circuitry 36, e.g., A channel 100 as shown in FIG. 4, in providing parameters of an atrial signal in order to distinguish FFRWs from P waves. FIG. 5A presents a series of curves. The top curve represents an unipolar digitized atrial signal, showing P wave and FFRW portions. The second curve represents the filter output, or SIG signal, relative to a negative threshold of 0.5 mV and a positive threshold of 0.5 mv; and illustrates minimum and maximum amplitude points. The third curve is the derived slope (SL) curve, with an indication of a negative threshold of 0.5 mV and a positive threshold of 0.5 mv. At the bottom the sense signal, the 50 ms sense window and 70 ms analysis window are indicated.

Figure 5B:
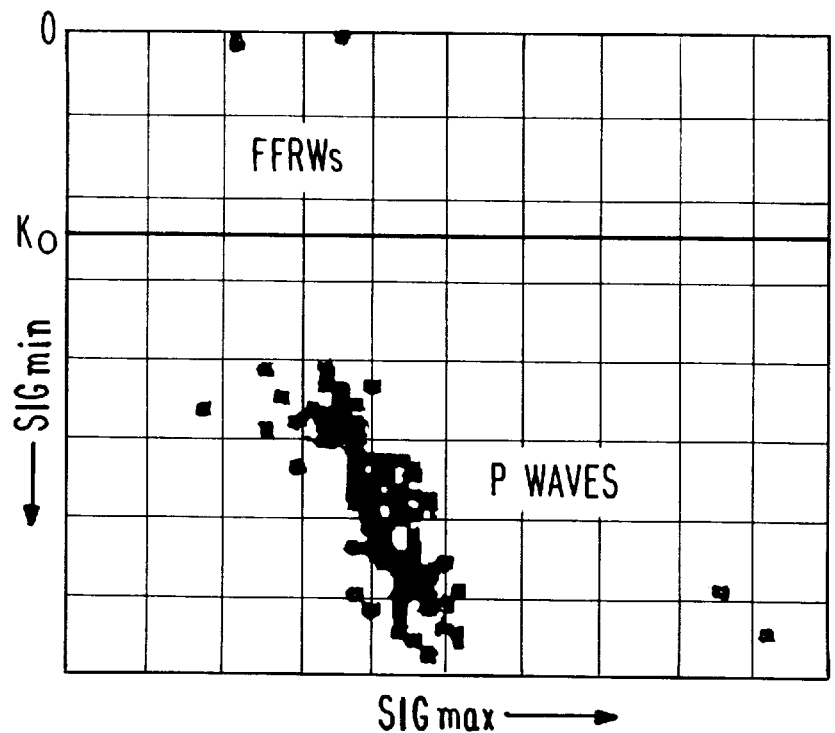
FIG. 5B is a plot of the minimum and maximum values of the filtered signal for a number of signals obtained from an atrial channel.
Figure 5C:
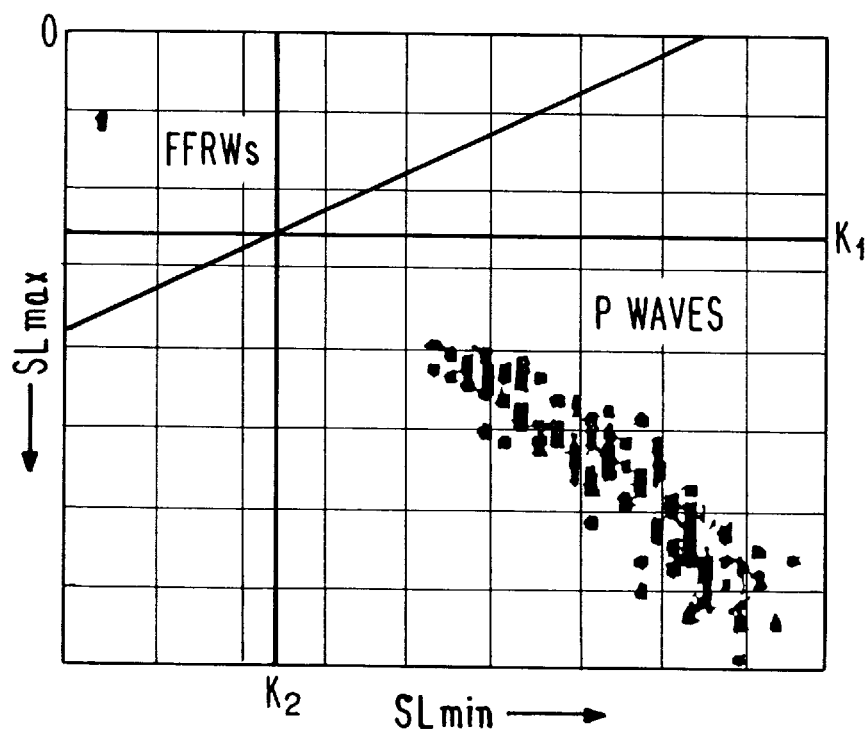
FIG. 5C is a plot of the minimum and maximum values of the slope signal for the same signals as illustrated in FIG. 5B.
Figure 5D:
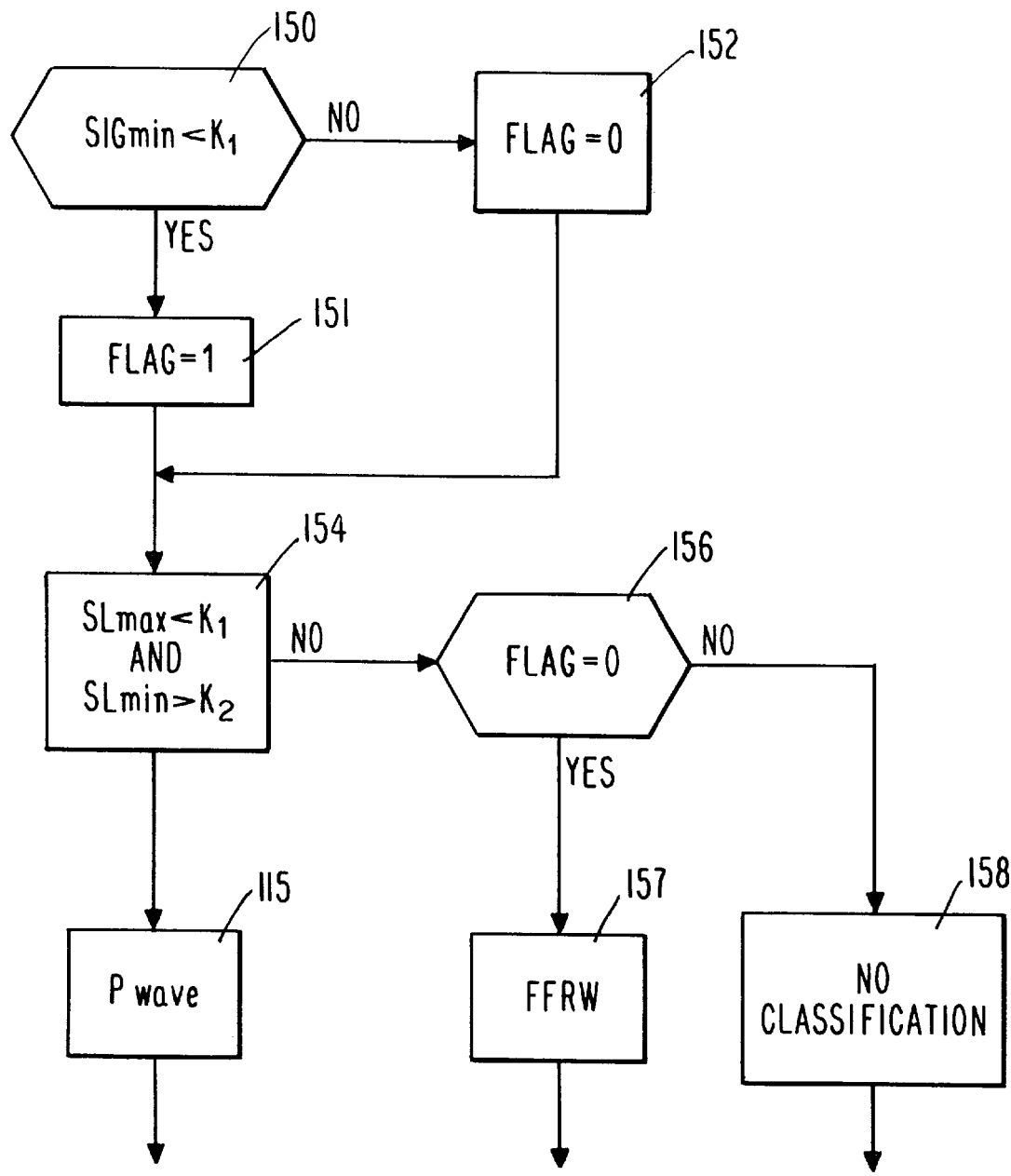
FIG. 5D is a flow diagram illustrating an algorithm for distinguishing between P waves and FFRWs, as used in operating on the parameter data illustrated in FIGS. 5B and 5C.

FIG. 5B is a plot of SIGmin and SIGmax signals, for a plurality of processed signals. It is seen from this that most of the signals have a SIGmin value which is below a predetermined horizontal line, i.e., below a predetermined value of SIGmin shown as $K_o$. In FIG. 5C, data from the same signals is plotted, comparing SLmax with SLmin. In this case, it is seen that P waves fall below a horizontal line shown as $K_1$, and to the right of vertical line $K_2$. That is, signals meeting these criteria have a characteristic of P waves, whereas signals that do not have a characteristic of FFRWs. By satisfying the criteria set forth by FIGS. 5B and 5C, P waves can be distinguished from FFRWs with great confidence. This is shown in the flow diagram of FIG. 5D, which is carried out by the microprocessor, e.g., block 108 of FIG. 4. At 150, it is determined whether SIGmin is less than $K_o$. If yes, at 151 the flag is set equal to 1, meaning that the analysis of the SIG signal alone suggests a P wave. If no, at 152 the flag is set equal to 0, corresponding to an initial analysis of an FFRW. At 154, the SL signal is compared to the SL criteria; if SLmax is less than $K_1$, and SLmin is greater than $K_2$, then at block 155 the signal is classified as a P wave. However, if the answer at 154 is no, the routine goes to 156 and inspects the flag to recall the outcome of the SIG analysis. If the flag is set to 0, then both the SIG and SL signals indicate an FFRW, and at 157 the signal is classified is an FFRW. However, if the flag had been set to 1, the result is ambiguous, and at 158 it is determined that there is no event classification.

Figure 6:
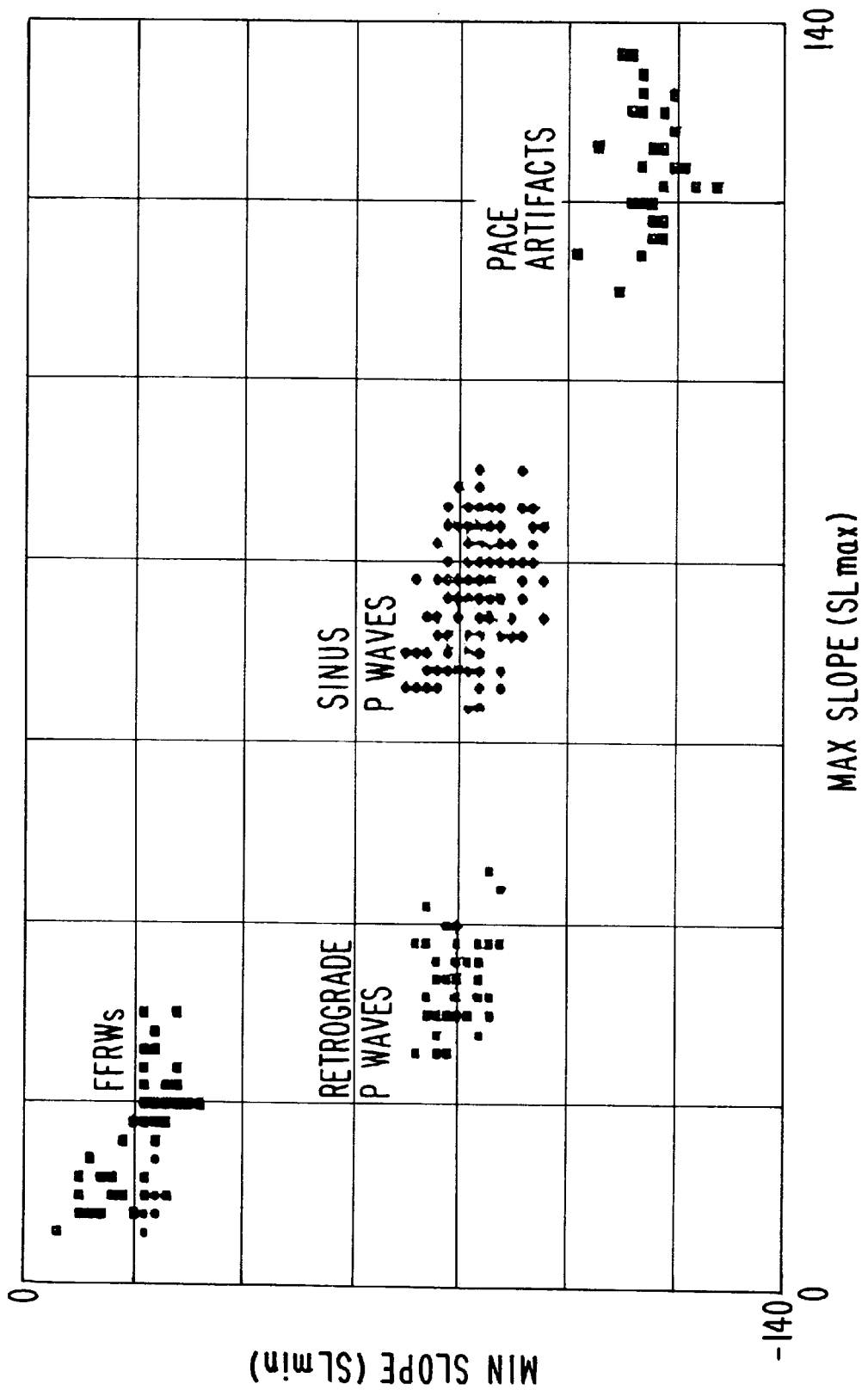
FIG. 6 is a plot of data representing slope minima and maxima, illustrating criteria for classifying atrial signals as FFRWs, retrograde P waves, sinus P waves and pace artifacts.

Referring now to FIG. 6, there is shown data relating to the SL signal, suggesting criteria for distinguishing FFRWs, retrograde P waves, sinus P waves and pace artifacts. Thus, if the magnitude of SLmin is less than 40, and SLmax is less than about 40, this data suggests classification as an FFRW. If the magnitude of SLmin is greater than 60 and SLmax is greater than 20 but less than 60, the signal appears to be a retrograde P wave. If the signal has an SLmin magnitude greater than 60 and less than 100; and an SLmax value greater than 60 but less than 100, it is suggested to be a normal or sinus P wave. And, if the SLmax value is greater than 100 the signal is suggested to be classified as a pace artifact. Thus, for a more sophisticated classification algorithm than that of FIG. 5D, these criteria can be incorporated. Also, although not shown in FIG. 6, PACs commonly have slope parameters different from normal sinus P waves, such that they can be distinguished by processing of a selected combination of the nine available parameters.

Figure 7A:
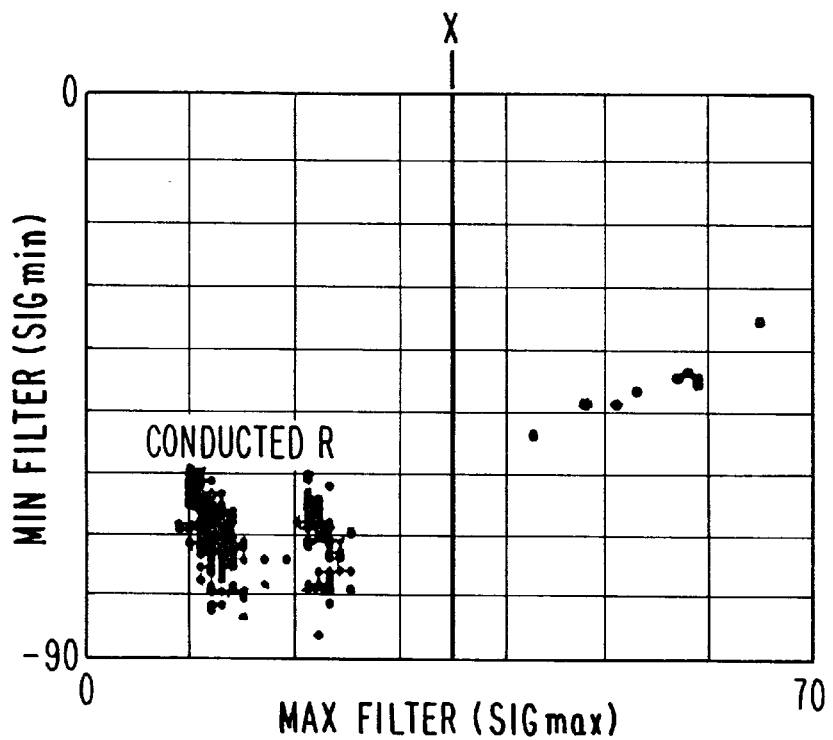
FIG. 7A is a plot of filtered signal data from a ventricle, illustrating criteria for distinguishing PVCs from normal conducted R waves.
Figure 7B:
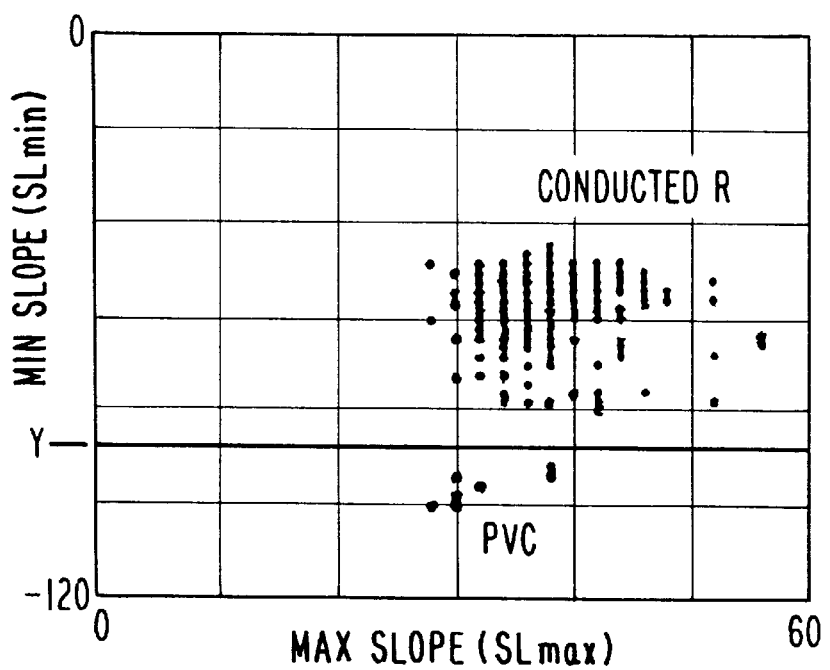
FIG. 7B is a plot of slope data from the ventricle, illustrating differences of PVCs and normal conducted R waves.
Figure 7C:
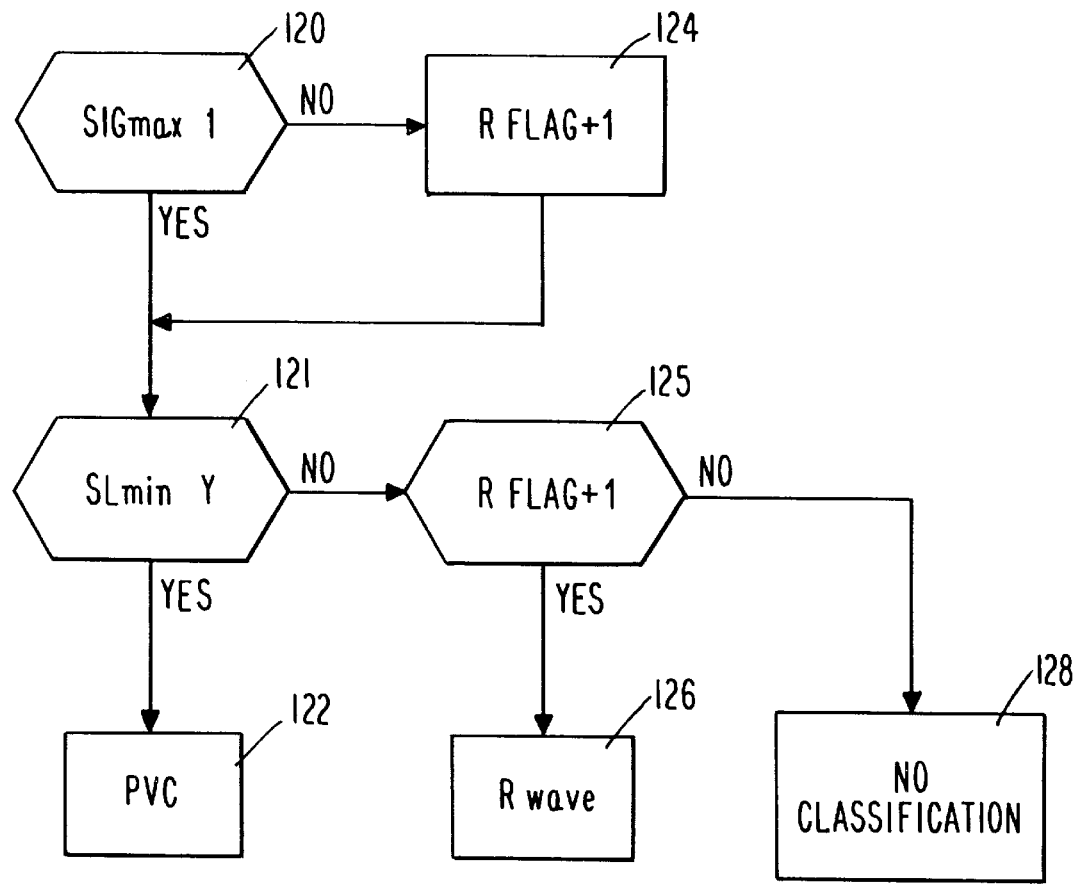
FIG. 7C is a flow diagram illustrating an algorithm for distinguishing PVCs from conducted R waves based upon criteria suggested by the above data.

Referring now to FIGS. 7A, 7B, 7C, there is illustrated the use of the invention for distinguishing PVCs from normal conducted R waves. FIG. 7A illustrates ventricular signal data, plotting SIGmin against SIGmax, while FIG. 7B plots SLmin against SLmax. FIGS. 7A and 7B suggest criteria for distinguishing a PVC from a conducted R wave, which criteria are utilized in the algorithm of FIG. 7C. As seen at block 120 and FIG. 7A, if SIGmax is greater than a constant X, this suggests the probability of the a PVC. If the comparison is positive, the routine goes to block 121 and compares the value of SLmin with the constant Y. As seen in FIG. 7B, if SLmin is greater than Y, this again suggests a PVC, and the routine goes to block 122 and classifies the event as a PVC. Returning to 120, if SIGmax is less than X, the routine goes to block 124 and sets the R flag=1. Then, if at 121 SLmin is found to be less than Y, the routine goes to block 125. If the R flag is already set to 1, this means that both criteria for an R wave are present, and the routine goes to block 126 and classifies the signal as an R wave. If the answer at 125 is no, at 128 the algorithm concludes that the situation is ambiguous, and there is no classification.

Figure 8A:
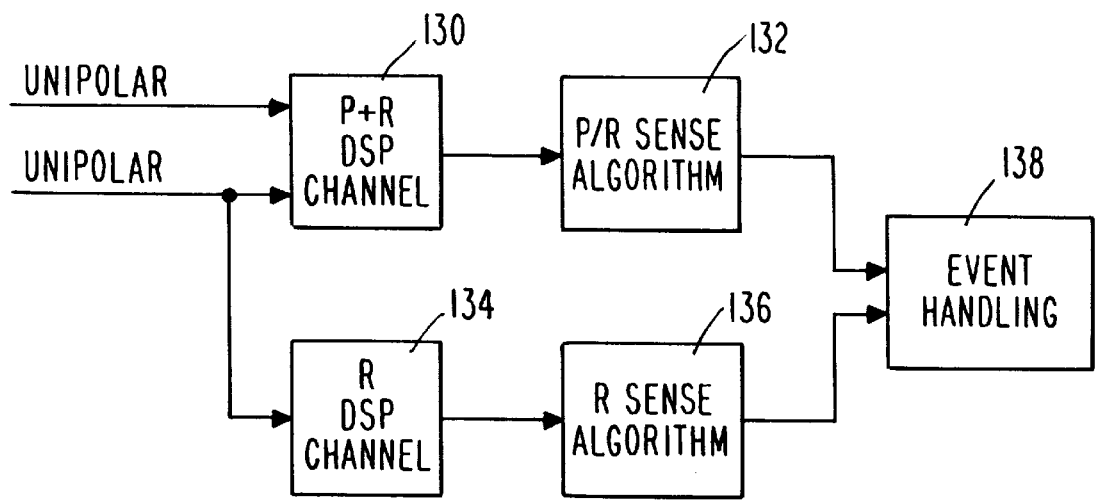
FIG. 8A is a block diagram illustrating a pacemaker in accordance with this invention utilizing combipolar sensing.
Figure 8B:
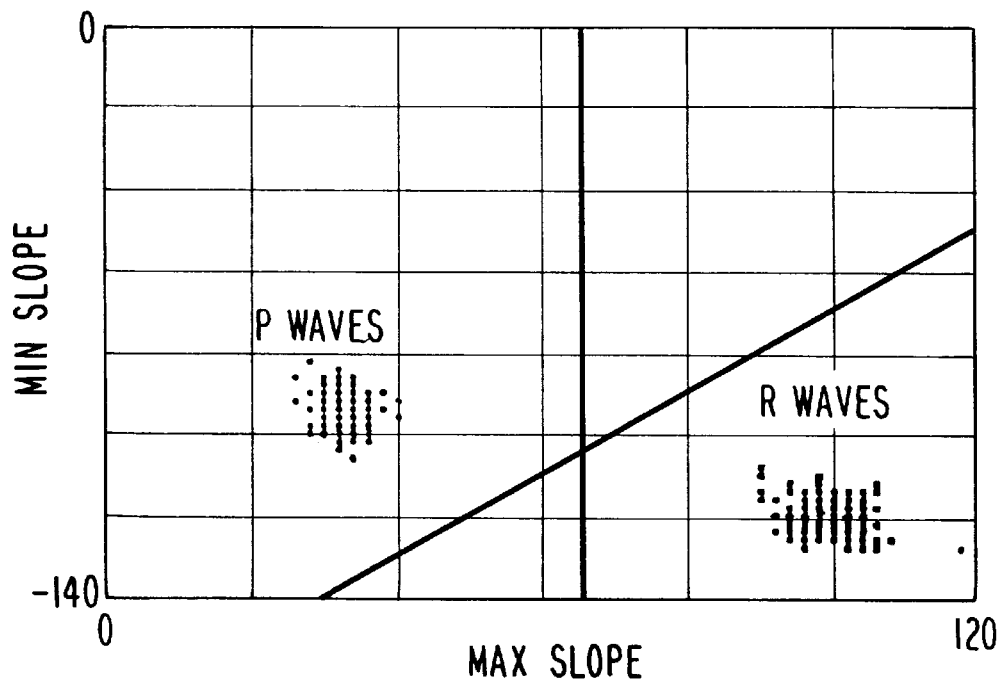
FIG. 8B is a plot illustrating slope data derived from combipolar signals.
Figure 8C:
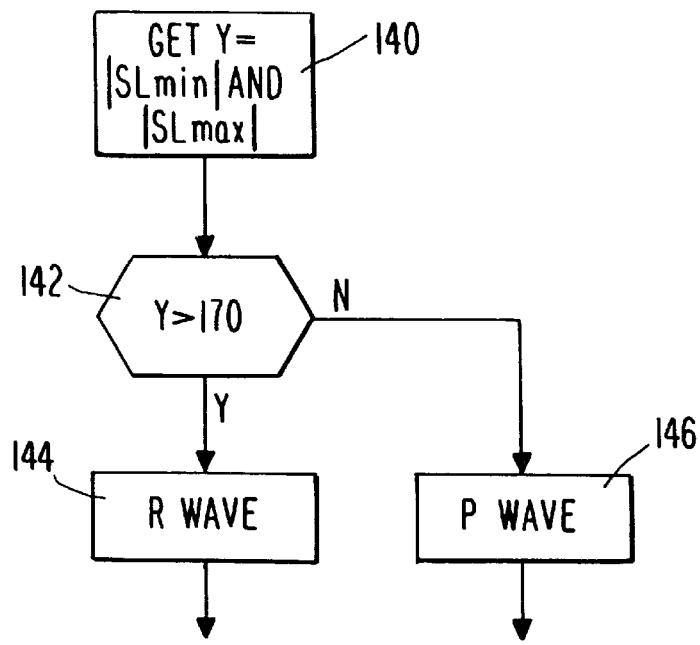
FIG. 8C is a simplified flow diagram illustrating an algorithm for distinguishing combipolar signals in terms of P waves and R waves.

Referring now to FIGS. 8A, B and C, there is illustrated the use of the combined DSP and software techniques of this invention with combipolar pacemaker sensing. As illustrated in FIG. 8A, this arrangement essentially provides bipolar differential sensing by means of an atrial unipolar lead and a ventricular unipolar lead. This arrangement is known to combine the advantages of bipolar sensing and unipolar leads, providing less interference by extraneous noise, and reduced sensing of myopotentials, FFRWs and other artifacts. The combined signals from the atrial and ventricular leads are inputted into channel block 130, designated P+R DSP channel. At the same time, the signal from the ventricular lead is inputted into the R DSP channel 134. The combined P+R sense and parameter signals are outputted from channel 130 and operated on by a P/R sense algorithm 132, which classifies the signal as a P wave or an R wave. Likewise, the sense and parameter signals from the R channel 134 are operated on by an R sense algorithm 136. Signals classified by either algorithm are sent for event handling. It is seen in FIG. 8B that P waves can be clearly demarcated from R waves by the diagonal line, which represents the sum of the magnitude of SLmin and SLmax. For this data, this sum is equal to 170, such that for any signal where the combined magnitude is less than 170, a P wave is indicated; whereas if the combined magnitudes are greater than 170, an R wave is indicated. As indicated at block 140 of FIG. 8C, in analyzing a sensed signal from the P+R channel, the algorithm first gets the sum of the magnitudes of the two slope parameters, at 140. At 142, it is determined whether this sum, indicated as Y, is greater than 170. If yes, the signal is classified as an R wave at 144; if no, it is classified as a P wave at 146. It is to be understood that while FIG. 8C presents logic steps limited to analyzing the slope parameters, the algorithm may additionally utilize any of the other parameters as shown in FIG. 3. Of course, where one parameter comparison, such as suggested by FIG. 8C, is seen to predict with a high confidence, it is weighted more than other comparisons. However, in general, one or more criteria can be combined on a logical AND or OR basis in the classification algorithm.

I claim:

1. A cardiac pacing system having a pacemaker and lead means for interconnecting said pacemaker and the patient's heart, said pacemaker having pulse means for generating pacing pulses and control means for controlling the operation of said pacemaker, said lead means having electrode means for delivering pacing pulses to a patient's heart and for sensing cardiac signals, said pacemaker having DSP means for amplifying and processing said cardiac signals sensed by said electrode means, and classifying means for classifying sensed cardiac signals, said DSP means comprising at least one DSP channel, said channel comprising:

conversion means for converting said received amplified signals to digital signals;

digital filter means for filtering said converted signals to provide filtered signals;

slope means for operating on said filtered signals to provide slope signals representative of the slope of said filtered signals;

sense means for determining from said filtered signals and said slope signals whenever a cardiac event is detected, and the sense time of each said detection;

analysis window means for timing out an analysis window of predetermined duration following or preceding a said sense time;

parameter means for processing said filtered signals and said slope signals during said analysis window, and for generating from said processing a plurality of respective parameters from said signals; and wherein said pacemaker further comprises classification means for receiving said parameters from said DSP means and for classifying each said signal as a function of said parameters.

2. The system as described in claim 1, wherein said pacemaker comprises a microprocessor and said classification means comprises said microprocessor and an algorithm for operating upon said parameters.

3. The system as described in claim 2, wherein said electrode means comprises means for a plurality of respective intracardiac signals, and wherein said DSP means comprises a plurality of said channels, each channel corresponding to a respective one of said intracardiac signals, and wherein said classification means comprises a plurality of respective programmable algorithms for processing the parameters generated by each said channel.

4. The system as described in claim 1, wherein said conversion means comprises a delta-sigma modulator circuit, and wherein DSP means further comprises interconnection means for interconnecting said conversion means, said digital filter means, said slope means, said sense means and said parameter means.

5. The system as described in claim 1, wherein said parameter means comprises means for deriving four parameters from said filtered signal during each said analysis window and for deriving four respective parameters from said slope signal during each said analysis window, and wherein said classification means comprises means for classifying each said sensed signal as a function of said four signal parameters and said four slope parameters.

6. The system as described in claim 5, wherein said parameter means further comprises means for deriving a signal length as a function of comparing said filtered signals and said slope signals to predetermined threshold criteria.

7. The system as described in claim 1, wherein said sense means comprises means for comparing said filtered signals with at least one predetermined threshold and for comparing said slope signals with at least another predetermined threshold.

8. The system as described in claim 7, wherein said sense means comprises means for determining when the magnitude of said filtered signals has exceeded said one predetermined threshold and the magnitude of said slope signals has exceed said another threshold within a predetermined time interval.

9. The system as described in claim 1, wherein said parameter means comprises means operative during said analysis window for determining a minimum and maximum value for said filtered signals and for said slope signals.

10. The system as described in claim 9, wherein electrode means comprises means for sensing atrial signals, and said classifying means comprises means for distinguishing P waves and FFRS waves as a function of said minimum and maximum values for said filtered signals.

11. The system as described in claim 10, wherein said classifying means comprises means for distinguishing P waves and FFRS waves as a function of the sum of the slope maximum and minimum absolute values during a said analysis window.

12. The system as described in claim 10, wherein said classifying means comprises stored criteria relating to retrograde P waves, and comprises a software algorithm for distinguishing retrograde P waves from natural sinus P waves by comparing said minimum and maximum values to said criteria.

13. The system as described in claim 10, wherein said classifying means comprises means for distinguishing FFRWs, retrograde P waves, PACs and sinus P waves.

14. The system as described in claim 9, wherein said electrode means comprises means for sensing ventricular signals, and wherein said classifying means comprises means for classifying PVCs.

15. A cardiac pacing system, having a pulse generator for generating pacing pulses and lead means for delivering said pacing pulses to a patient's heart and for sensing intracardiac signals from said patient's heart, and control means for controlling the operation of said pulse generator as a function of sensed intracardiac signals, said control means comprising:

a DSP circuit having a plurality of channels, each said channel having processing means for determining when a said intracardiac signal has occurred and for processing said signal to generate a plurality of signal parameters, and each said channel being programmable and having data stored therein for use in sensing and classifying a respective type of intracardiac signal;

microprocessor means for operating on each said plurality of signal parameters to classify the signal that has occurred, said microprocessor means having a respective programmable signal algorithm corresponding to each of said DSP channels and operating means for selecting the signal algorithm corresponding to the channel which has determined a signal occurrence and for classifying the signal that has occurred; and handling means for handling pacemaker operation in response to each type of signal which has occurred.

16. The system as described in claim 15, wherein said processing means comprises an analyzing means for each said channel, said analyzing means comprising analysis window means for timing out an analysis window during which signal parameters are obtained.

17. The system as described in claim 16, wherein said analyzing means comprises means for obtaining the slope of said signal, and means for determining maximum signal deviations for said signal and said slope during said analysis window.

18. The system as described in claim 17, wherein said analyzing means comprises signal max means for obtaining the maximum positive deviation of said signal during said analysis window and for obtaining the maximum negative deviation of said signal during said analysis window.

19. The system as described in claim 18, wherein said analyzing means comprises slope max means for obtaining the maximum positive deviation of said slope during said analysis window and for obtaining the maximum negative deviation of said signal during said analysis window.

20. The system as described in claim 17, wherein said analyzing means comprises means for obtaining up to 9 parameters reflective of a signal event, and the corresponding signal algorithm has means for classifying the event as a function of said up to 9 parameters.

21. The system as described in claim 20, wherein said analyzing means comprises means for obtaining a parameter (W) representative of the time from the first crossing of a threshold to the last threshold crossing.

* * * * *